US012246158B2

(12) United States Patent
Fiorino et al.

(10) Patent No.: US 12,246,158 B2
(45) Date of Patent: Mar. 11, 2025

(54) CONTROL VALVE FOR A LIQUID CIRCULATING IN A FLEXIBLE TUBE

(71) Applicant: I-SEP, Nantes (FR)

(72) Inventors: Adrien Fiorino, Nantes (FR); Sylvain Picot, Caluire Et Cuire (FR)

(73) Assignee: I-SEP (FR)

( * ) Notice: Subject to any disclaimer, the term of this patent is extended or adjusted under 35 U.S.C. 154(b) by 445 days.

(21) Appl. No.: 17/776,097

(22) PCT Filed: Nov. 10, 2020

(86) PCT No.: PCT/FR2020/052057
§ 371 (c)(1),
(2) Date: May 11, 2022

(87) PCT Pub. No.: WO2021/094685
PCT Pub. Date: May 20, 2021

(65) Prior Publication Data
US 2022/0378987 A1 Dec. 1, 2022

(30) Foreign Application Priority Data
Nov. 12, 2019 (FR) ..................... 1912617

(51) Int. Cl.
*A61M 39/28* (2006.01)
*A61M 1/02* (2006.01)
*F16K 7/06* (2006.01)

(52) U.S. Cl.
CPC ........... *A61M 39/285* (2013.01); *F16K 7/065* (2013.01); *A61M 1/02* (2013.01)

(58) Field of Classification Search
CPC .... A61M 39/285; A61M 39/26; A61M 39/28; A61M 1/02; A61M 2205/3334;
(Continued)

(56) References Cited

U.S. PATENT DOCUMENTS 2,556,689 A * 6/1951 Grove ..................... F16K 7/065
251/7
3,016,915 A * 1/1962 Moeller, Jr. ............ F16K 7/065
251/9
(Continued)

FOREIGN PATENT DOCUMENTS

CN 203469131 U 3/2014
EP 0624382 A1 11/1994
(Continued)

OTHER PUBLICATIONS

International Search Report for PCT/FR2020/052057 dated Apr. 29, 2021. 4 pgs.

*Primary Examiner* — Kenneth Rinehart
*Assistant Examiner* — Jonathan J Waddy
(74) *Attorney, Agent, or Firm* — Lerner David LLP (57) ABSTRACT

The invention relates to an automatic valve for regulating a flow rate of liquid intended to circulate in a flexible tube, comprising:
 a cam system (23) mounted moveably on a base and rotationally around an axis of rotation,
 a bearing part (24) translationally mounted on the base, arranged to be translationally moved as a result of a rotational movement of the cam system (23), and comprising a compression portion (240),
 an abutment part (25) positioned opposite the compression portion (240), defining with the bearing part (24) a receiving space intended to receive a flexible tube (3), the translation of the bearing part (24) displacing the compression portion (240) along the direction of translation, in order to modify a dimension of the receiving space,
 a magnet and a magnetic sensor detecting the magnetic field generated by the magnet.

24 Claims, 7 Drawing Sheets

(58) Field of Classification Search
CPC ..... F16K 7/02; F16K 7/04; F16K 7/06; F16K 7/065; G01D 5/142
USPC ........................................................ 251/7, 8
See application file for complete search history.

(56) References Cited

U.S. PATENT DOCUMENTS

| | | | | |
|---|---|---|---|---|
| 4,360,007 | A | * | 11/1982 | Levy .................... A61M 39/285 |
| | | | | 128/DIG. 25 |
| 4,715,517 | A | * | 12/1987 | Potter .................. B67D 7/0205 |
| | | | | 222/212 |
| 5,098,060 | A | * | 3/1992 | Mogler .................... F16K 7/065 |
| | | | | 251/251 |
| 5,221,268 | A | * | 6/1993 | Barton .............. A61M 5/16813 |
| | | | | 604/246 |
| 7,980,425 | B2 | * | 7/2011 | Baron .................. B67D 1/1231 |
| | | | | 137/256 |
| 2003/0229302 | A1 | * | 12/2003 | Robinson ............. A61M 1/0218 |
| | | | | 604/4.01 |
| 2005/0053501 | A1 | * | 3/2005 | Akahori ............ F16K 31/52491 |
| | | | | 417/474 |
| 2005/0245873 | A1 | | 11/2005 | Nemoto |
| 2013/0074938 | A1 | * | 3/2013 | Chen ...................... E03C 1/0412 |
| | | | | 137/551 |
| 2017/0108121 | A1 | * | 4/2017 | Kuhns ...................... F16H 25/20 |
| 2019/0085875 | A1 | * | 3/2019 | Slama ....................... G01D 5/12 |
| 2021/0052789 | A1 | | 2/2021 | Gadrat et al. |
| 2023/0218883 | A1 | * | 7/2023 | Naples .................. A61M 39/28 |
| | | | | 604/48 |

FOREIGN PATENT DOCUMENTS

| | | |
|---|---|---|
| EP | 1541184 A1 | 6/2005 |
| FR | 2379290 A1 | 9/1978 |
| FR | 3076222 A1 | 7/2019 |
| WO | 2019129973 A1 | 7/2019 |
| WO | 2019129974 A1 | 7/2019 |

* cited by examiner

CONTROL VALVE FOR A LIQUID CIRCULATING IN A FLEXIBLE TUBE

CROSS-REFERENCE TO RELATED APPLICATIONS

The present application is a national phase entry under 35 U.S.C § 371 of International Application No. PCT/FR2020/052057 filed Nov. 10, 2020, which claims priority from French Application No. 1912617, filed Nov. 12, 2019, all of which are hereby incorporated herein by reference.

FIELD OF THE INVENTION

The present invention relates to the field of the regulation of fluids, in particular liquids, circulating in flexible tubes. More specifically, the invention pertains to a valve for regulating fluid circulating in a flexible tube. The present invention finds a particularly advantageous application for medical applications. The invention may more particularly fall within the field of treatment of haemorrhagic liquid, notably for an autotransfusion of blood into a patient.

PRIOR ART

Autotransfusion or autologous transfusion, namely the transfusion into a patient of his or her own blood, is increasingly practiced during surgical interventions since it avoids the incompatibilities that may exist with homologous or allogenic transfusions. Autotransfusion avoids in addition transmission of infectious diseases.

The treatment of blood during an autotransfusion consists firstly in withdrawing blood from the patient and in anticoagulating it during the withdrawal. Indeed, it is necessary to control the coagulating activity of the blood to avoid the formation of blood clots which would prevent the correct recovery of the red blood cells present in the blood. The withdrawn blood must next be subjected to a treatment such as a filtration, to separate a liquid phase from a phase containing the cells of interest (red blood cells, thrombocytes, etc.).

Systems for treating haemorrhagic liquid during an autotransfusion implementing membrane filtration have been developed. One advantage of membrane filtration treatment systems is to enable conservation of red blood cells and thrombocytes, unlike centrifugation for example. Tangential filtration devices are notably used, in order to avoid clogging of the filtration membranes by the cells of interest.

Systems for treating haemorrhagic liquid must be able to be used in a context of life or death emergency for the patient. It is necessary that the blood withdrawal, treatment and reinjection times are very short, while guaranteeing good blood treatment efficiency. For example, for a collected blood volume of 500 millilitres, it is preferable that the treatment time is less than 10 minutes, preferably comprised between 4 and 6 minutes.

It is thus necessary that the commands for circulating liquid within the different tubings of the treatment system, for example at the level of the fluid inlets/outlets of a membrane filtration device and the fluid inlets/outlets of a blood treatment bag, are very reactive, reliable and efficient. It is wished in particular to control easily the flow of haemorrhagic liquid, cleaning liquid, or other fluids within the fluid circulation paths of the treatment system.

Systems for treating haemorrhagic liquid known from the prior art integrate, as liquid flow regulating members, electrically actuated valves operating with electromagnets. The electrically actuated valves control the section of the tubings forming the fluid circulation paths, and thus control the flow rate of liquid through the tubing.

This mode of controlling the liquid flow rates does not however give entire satisfaction. A first drawback of a solenoid valve with electromagnet is that the powering off of the solenoid valve is liable to modify the opening/closing state of the solenoid valve, since the electromagnet is cut off. It would be desirable to have available a flow regulating member of which the opening/closing state is not modified when it is powered off.

Further, the electromagnet must be dimensioned to be able to exert an important mechanical force in order to open or to close the fluid circulation path. The electromagnet thus has a high consumption of electrical energy and has important dimensions, being able to make the solenoid valve bulky.

Liquid flow regulating members within a tubing comprising compressed air systems are also known. However, the use of such regulating members necessitates including a compressor in the system for treating haemorrhagic liquid. The presence of escapes of pressurised air in the operating theatre proves to be problematic, because these escapes generate a sound nuisance and risks of contamination within the operating theatre.

Finally, liquid flow regulating members known from the prior art generally do not integrate means enabling a simple determination in real time of their opening/closing state at a given instant. Yet, in a treatment system used in autotransfusion, it is important to have access at any instant to the opening/closing state of each liquid flow regulating member.

GENERAL DESCRIPTION OF THE INVENTION

In view of the above, there exists a need for improved liquid flow regulating members, to be able to be integrated notably in liquid treatment systems, notably haemorrhagic liquid treatment systems. More specifically, there exists a need for liquid flow regulating members enabling a rapid, reactive and efficient control of the flow rate of liquid in the tubing.

More particularly, there exists a need for a liquid flow regulating member that can be switched over very rapidly between an open position, in which liquid circulates with a high flow rate in the tubing, and a closed position, in which the flow is blocked. The sought after flow regulating member is preferably capable of being stabilised in any intermediate position between the open position and the closed position, notably a position in which the liquid circulates in the tubing with a low, but not zero, flow rate.

There exists an additional need for a flow regulating member having a functionality of detecting, in real time, the position of the regulating member. Indeed, in a system for treating haemorrhagic liquid for example, several liquid flow regulating members are commanded simultaneously and it is important to have access, at any instant, to the state of each of the liquid flow regulating members.

There exists an additional need for a flow regulating member that remains static after its powering off and does not change position.

The sought after flow rate regulating member is preferentially not very bulky. Notably, the elements enabling the detection in real time of the position of the regulating member preferably do not generate more bulk, and are preferably of simple design.

In this respect, according to a first aspect a valve for regulating a flow rate of liquid intended to circulate in a flexible tube is proposed, the regulating valve comprising:
- a valve base,
- a cam system arranged to be rotationally driven by a drive shaft of a motor, the cam system being moveably mounted on the valve base to rotate around an axis of rotation,
- a bearing part translationally mounted on the valve base, the bearing part being arranged to be translationally moved with respect to the valve base along a direction of translation following a rotational movement of the cam system, the bearing part comprising a compression portion,
- an abutment part mounted on the valve base and positioned opposite the compression portion along the direction of translation, such that the abutment part and the bearing part define between them a receiving space extending along a longitudinal direction and intended to receive a flexible tube,
- the translation of the bearing part displacing the compression portion along the direction of translation, in order to modify a dimension along the direction of translation of the receiving space formed between the bearing part and the abutment part.

The regulating valve according to the first aspect constitutes a very efficient and reactive automatic member for the regulation of the flow rate of liquid within the tube.

The flow rate of liquid is reduced or cancelled when the compression portion is displaced in the direction of the receiving space of the tube, and comes to bear against the outer wall of the tube so as to deform the inner volume of the tube. The abutment part blocks the tube along the direction of translation, on the side opposite to the compression portion. It is thus possible to compress the walls of the tube.

The translation of the compression portion, in the direction of the tube receiving space, is triggered by the rotation of the cam system, the latter being itself due to the movement of the drive shaft by the motor.

In the case where the compression portion bears against the abutment part and compresses the outer wall of the tube, the flow rate of liquid within the tube may be greatly reduced. A total occlusion of the tube may be reached, in which case the flow rate of liquid is completely interrupted, the regulating valve being in closed position.

One advantage of the proposed regulating valve is thus to enable a very rapid transition between an open state and a closed state, optionally passing through an intermediate state, in which liquid can circulate in the tubing with a lower flow rate compared to the flow rate obtained with the open state of the valve. The valve being able to be stabilised in said intermediate state, it is possible to obtain such a low flow rate through the tube in a controlled manner, for a desired duration.

Further, the regulating valve according to the first aspect is of simple design. For the movement of the cam system and the displacement of the bearing part, a very simple motor, for example a stepper motor of moderate dimensions, may suffice.

Optional and non-limiting characteristics of the regulating valve according to the first aspect are the following, taken alone or in any technically possible combinations thereof:
- the bearing part is translationally moveable along the direction of translation between the following two positions:
  - a close together position, in which the dimension of the receiving space along the direction of translation is equal to a first distance,
  - and a spaced apart position, in which the dimension of the receiving space along the direction of translation is equal to a second distance strictly greater than the first distance.
- the bearing part is configured to be stabilised in any intermediate position situated between the close together position and the spaced apart position.
- the regulating valve is an automatic valve.
- the compression portion is displaced in order to regulate a flow rate of liquid traversing the flexible tube.
- the cam system comprises a cylindrical member rotationally mounted around the axis of rotation and having an axis of revolution that is different from the axis of rotation.
- the bearing part comprises an inner wall defining a cavity, the cavity being provided to receive the cam system bearing against the inner wall.
- the cavity defined by the inner wall is oblong.
- the compression portion projects with respect to the bearing part along the direction of translation.
- the compression portion has a tip shape, and comprises a tip edge extending perpendicularly to the longitudinal direction and perpendicularly to the direction of translation.
- the abutment part comprises an abutment portion positioned facing the compression portion along the direction of translation, the compression portion and the abutment portion having surfaces of complementary shape.
- the abutment part comprises a projecting portion positioned facing the compression portion along the direction of translation, said projecting portion projecting with respect to the abutment part along the direction of translation.
- the regulating valve further comprises a magnet integral with the bearing part or integral with the valve base, and also comprises a magnetic sensor integral with the valve base, respectively integral with the bearing part, the magnetic sensor being arranged to detect a magnetic field generated by the magnet whatever the position of the bearing part.
- the magnet is positioned inside the bearing part.
- the magnet extends along a direction of extension perpendicular to the direction of translation of the bearing part.
- the magnet is a permanent magnet formed of a ferromagnetic material.
- the magnetic sensor comprises a Hall effect probe.
- the Hall effect probe comprises a thin plate.
- the magnet extends along a direction of extension perpendicular to a plane of extension of the thin plate.
- the abutment part is translationally mounted on the valve base along the direction of translation, the valve further comprising return means arranged to force the abutment part in the direction of the bearing part.
- the return means comprise a compression spring having a capacity greater than three kilogrammes.
- the valve base comprises two sides positioned opposite one another, said sides forming a guiding rail in which the bearing part is arranged to slide.
- the valve further comprises a cover intended to obstruct the receiving space as a function of the position of the bearing part.
- said cover is fixed on the cam system.

the cam system comprises a lateral face extending in a plane perpendicular to the axis of rotation of the cam system, said cover being fixed on the lateral face.

the cover comprises at least one straight edge and further comprises at least one rounded edge, and the abutment part has a shoulder complementary with the rounded edge.

the cam system comprises a centring pin and the cover comprises a centring cavity able to receive the centring pin.

the bearing part is translationally moveable along the direction of translation from the spaced apart position or from the close together position, to reach an intermediate travel position, in which the dimension of the receiving space along the direction of translation is equal to a third distance comprised between the first distance and the second distance, the bearing part being configured to be stabilised in the intermediate travel position.

the bearing part is translationally moveable along the direction of translation from the intermediate travel position or from the spaced apart position, to reach a supplementary intermediate travel position, situated between the intermediate travel position and the spaced apart position, the bearing part being configured to be stabilised in the supplementary intermediate travel position.

in the case where the regulating valve is provided with a cover, in the spaced apart position, the cover is positioned axially set back with respect to or flush with the compression portion along the direction of translation, so as not to obstruct the receiving space.

in the case where the regulating valve is provided with a cover, in the intermediate travel position and in the close together position, the cover extends at least partially over an axial extension comprised between the compression portion and the abutment part along the direction of translation, so as to prevent accidental removal of the flexible tube from the receiving space.

an amplitude of total angular displacement of the cam system around its axis of rotation, between the spaced apart position of the compression portion and the close together position of the compression portion, is comprised between 160 degrees and 200 degrees and is preferentially equal to around 180 degrees.

According to a second aspect, a unit for treating a haemorrhagic liquid taken from a patient with a view to an autotransfusion is proposed, the treatment unit comprising:

a filtration device configured to treat a haemorrhagic liquid by removing undesirable compounds from the haemorrhagic liquid, a treatment bag configured to contain a treated haemorrhagic liquid, at least one fluid transfer line enabling a circulation of fluid, the fluid transfer line fluidically connecting one among the filtration device and the treatment bag to a fluid inlet, or to a fluid outlet, or to the other among the filtration device and the treatment bag, the fluid transfer line being provided with at least one valve for regulating the flow rate of liquid such as defined above arranged for a regulation of a flow rate of liquid in the fluid transfer line.

Optional and non-limiting characteristics of the unit for treating haemorrhagic liquid according to the second aspect are the following, taken alone or in any technically possible combinations thereof:

the treatment unit comprises several fluid transfer lines comprising at least one liquid flow rate regulating valve, said fluid transfer lines being chosen from among: an intake line, a discharge line, a recirculation line, a transfusion line, a cleaning line, and a dilution line.

the magnetic sensor of the regulating valve is configured to produce a magnetic field detection signal, and the treatment unit further comprises a calculating unit configured to control a parameter of opening/closing of the regulating valve as a function of the magnetic field detection signal.

the calculating unit is configured to save in a memory, during a phase of starting up the treatment unit, an initial value of the magnetic field detection signal, the calculating unit being further configured to determine the opening/closing parameter as a function of said initial value during a later phase of operation of the treatment unit.

GENERAL DESCRIPTION OF THE FIGURES

Other characteristics, aims and advantages of the invention will become clear from the description that follows, which is purely illustrative and non-limiting, which should be read with regard to the appended figures, among which:

FIG. 3a is a partial perspective view of the regulating valve of FIG. 1a, wherein a portion of a valve base has been omitted to allow other elements to appear, this view corresponding to the state of the regulating valve in FIG. 1a.

DETAILED DESCRIPTION OF EMBODIMENTS OF THE INVENTION

In all of the figures and throughout the description hereafter, similar elements bear identical alphanumeric references.

In the description that follows, "haemorrhagic liquid" is taken to mean a liquid resulting from flow from a blood vessel, notably from blood. "Fluid" is more generally taken to mean a deformable substance, which flows under its own weight.

Liquid Flow Rate Regulating Valve

In appended FIGS. 1a to 1d is represented a liquid flow rate regulating valve 2 associated with a tubing 3, for example a flexible tube, the valve being seen from the side and represented in four distinct opening/closing states which will be described hereafter. The valve 2 is intended to regulate a flow rate of fluid circulating within the tubing 3.

Figure 2:
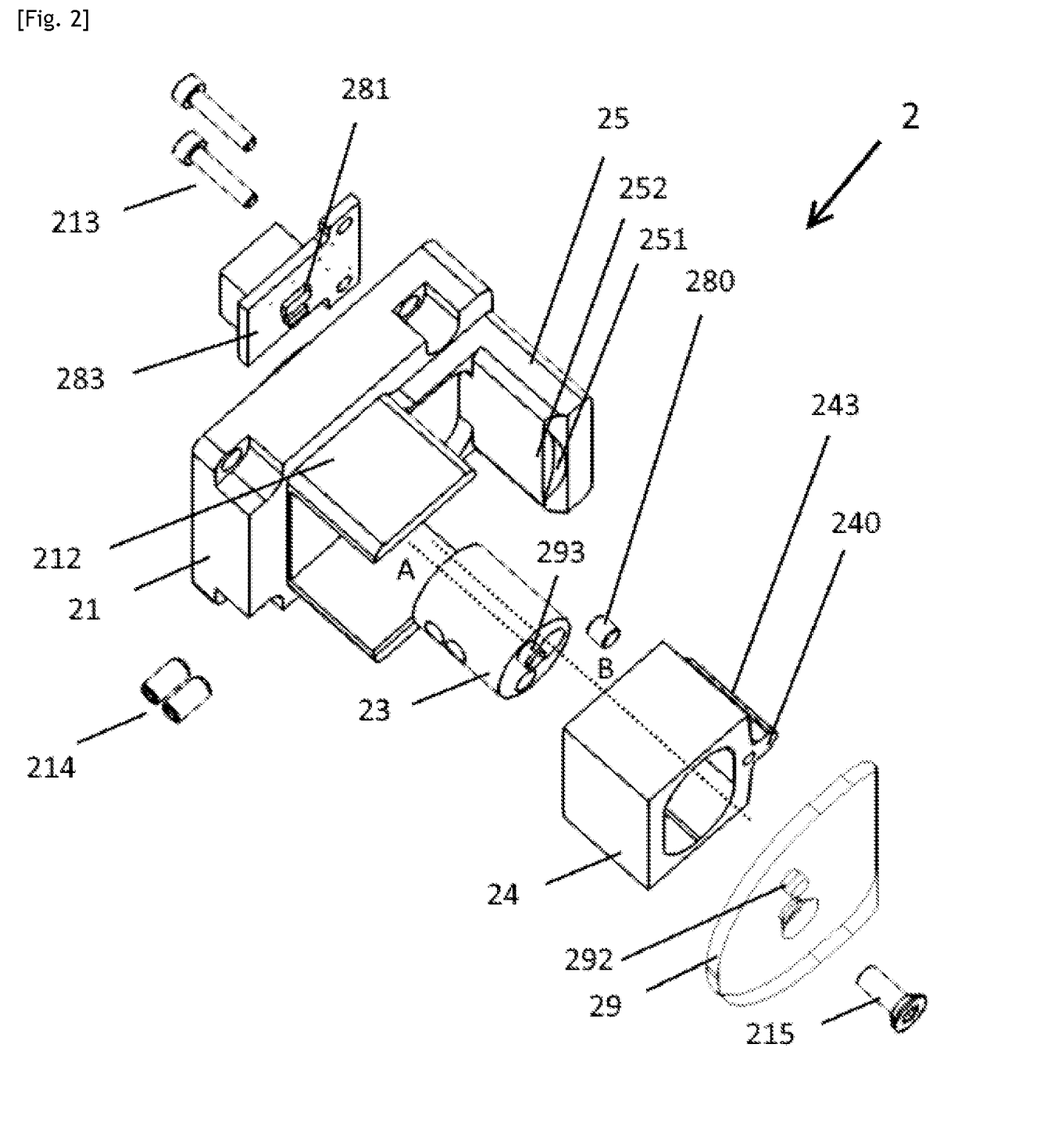
FIG. 2 is an exploded top view of the regulating valve of FIGS. 1a to 1d.

In FIG. 2 the same regulating valve 2 is represented, without associated tubing, in exploded view along an axis of rotation B of a cam system of the valve, to illustrate internal components of the valve 2.

Figure 1A:
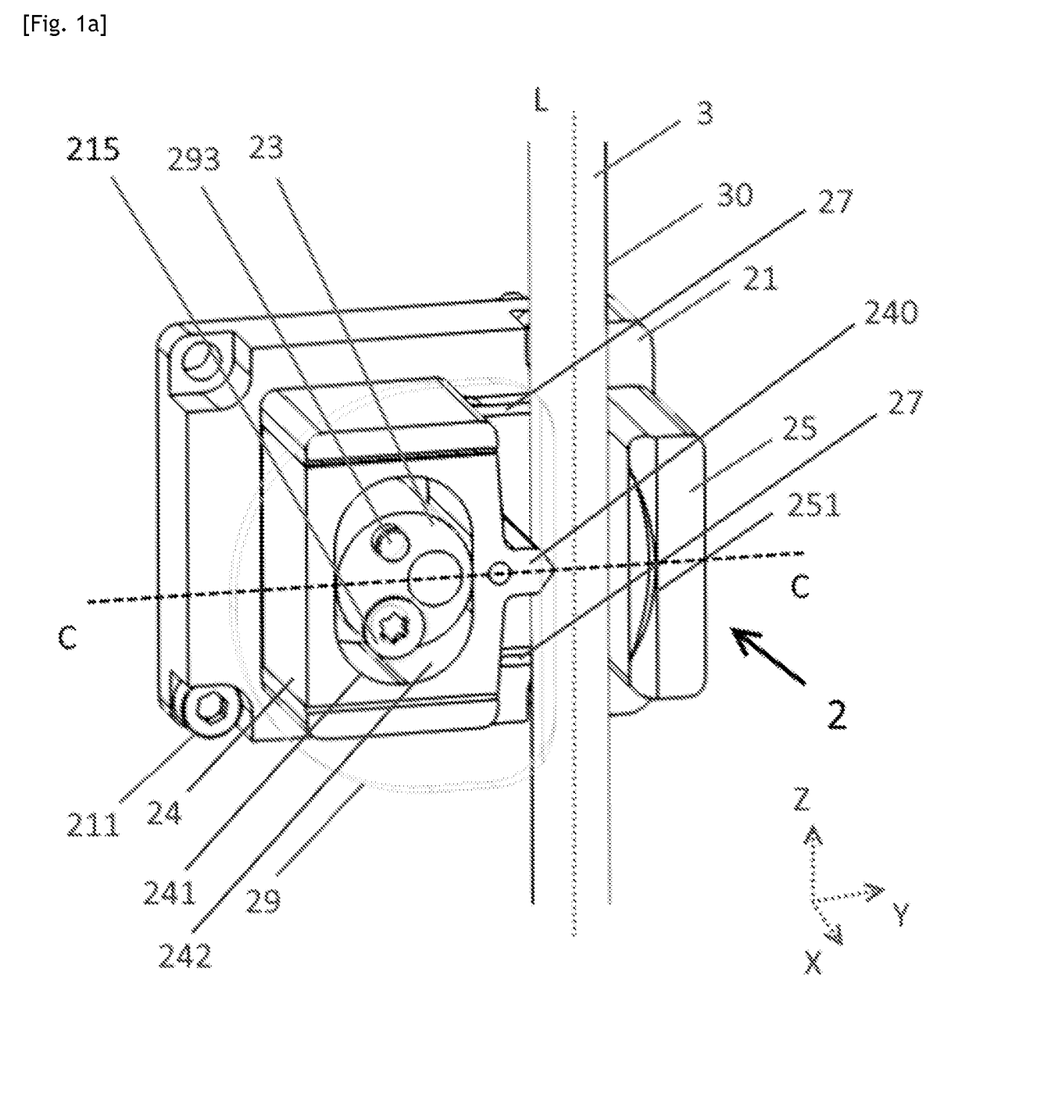
FIG. 1a is a perspective view of a liquid flow rate regulating valve according to one embodiment of the invention, this figure corresponding to a position of opening of the regulating valve. The regulating valve here represented may be integrated in a treatment unit according to FIG. 5.

The tubing 3 here has a general hollow cylindrical shape. The tubing 3 extends along a longitudinal direction L parallel to a direction bearing the reference Z in FIGS. 1a to 1d. The direction Z is illustrated in FIG. 1a in vertical position.

The tubing 3 is intended to be positioned in a receiving space defined by mechanical elements of the valve 2. The receiving space is variable as a function of an opening/closing state of the valve, as will be seen in the description hereafter.

As an example, the tubing 3 may have an inner wall (not illustrated) of diameter comprised between 1 millimetre and 5 millimetres, for example 2.5 millimetres, and an outer wall 30 of diameter comprised between 2 millimetres and 10 millimetres, for example 4 millimetres.

It will however be noted, in so far as the receiving space is of variable size, a tubing having walls of diameters different to the diameters indicated above may be used, with the same advantages, in association with the valve 2.

The regulating valve 2 notably comprises a valve base 21, a cam system 23, a bearing part 24 and an abutment part 25.

"Valve base" is taken to mean a set of elements intended to be fixed to a frame. For example, the valve base is fixed to a body of a support unit of a system for treating haemorrhagic liquid with a view to an autotransfusion. According to the example shown in FIG. 1, the valve base is fixed to a frame by screws 211. The valve base 21 has for example a general parallelepiped shape.

Cam System and Bearing Part

The cam system 23 is mounted on the valve base 21, while being rotationally moveable around an axis of rotation B (visible in FIG. 2) with respect to the valve base 21. The axis of rotation B is parallel to a direction X, perpendicular to the direction Z. The direction X is represented in FIG. 1a.

The cam system 23 is intended to be rotationally driven, around said axis of rotation B, by a drive shaft of a motor. The appended figures do not illustrate the drive motor or the drive shaft.

Any type of motor could be used for the adjustment of the angular position of the cam system 23, preferably a stepper motor (or stepper).

One advantage of the use of a motor to adjust the angular position of the cam system 23 is that, when the motor is powered off, the angular position of the cam system at the moment of powering off is conserved. A stepper motor is advantageous because it enables a precise control of the angular position of the drive shaft, and thus the angular position of the cam system 23.

The angular position of the drive shaft of the motor is, for example, controlled by a signal transmitted by a processor of a system for treating haemorrhagic liquid.

Preferably, the cam system 23 is positioned directly on the drive shaft, while being integral with the latter in its rotation around the axis of rotation B. In an alternative, an angle transmission may be produced between a longitudinal axis of the drive shaft and the axis of rotation of the cam system 23.

In the example of FIGS. 1a to 1d, the cam system is formed of a cylindrical member rotationally mounted around the axis of rotation B, and of which the axis of revolution A (visible in FIG. 2) is offset with respect to the axis of rotation B, while being parallel to this axis of rotation B. "Axis of revolution" is taken to mean an axis of symmetry of the longitudinal surface of the cylindrical member. The cylindrical member thus forms an eccentric wheel. For example, if the drive shaft directly drives the eccentric wheel, the longitudinal axis of the drive shaft is not merged with the axis of revolution A of the eccentric wheel.

The eccentric wheel is preferably maintained in position by maintaining screws, such as the screws bearing the reference 214 in the exploded view of FIG. 2.

The bearing part 24 is moveably mounted on the valve base 21, and arranged with respect to the cam system 23 in such a way that a rotational movement of the cam system 23 around its axis of rotation B drives a translational movement of the bearing part 24 along a direction of translation Y. The direction of translation of the bearing part 24 corresponds to the direction bearing the reference Y in FIGS. 1a to 1d.

The cam system 23 and the bearing part 24 here form an eccentric system.

The bearing part 24 has the function of exerting, in a controlled manner, a compressive force on the outer wall of the tubing 3 in order to reduce locally the section of the tubing 3.

In a preferential manner, the direction of translation Y of the bearing part 24 is perpendicular to the two directions X and Z. Thus, a compression caused on the tubing 3 by a translational displacement of the bearing part 24 can result in a rapid reduction of the section of the tubing 3, at the level of the zone of the tube facing the bearing part 24 along the direction of translation Y.

In the example of FIGS. 1a to 1d, the bearing part 24 is pierced by a cavity 242 in which is arranged the cam system 23 (namely the eccentric wheel in the example illustrated). The bearing part 24 and the cam system 23 are thus mechanically coupled. The cavity 242 is delimited by an inner edge 241 of the bearing part 24.

The cavity 242 preferably has a general oblong shape. Preferably, the inner edge 241 describes two opposite flat surfaces, which extend substantially parallel to the plane XZ. During its rotation, the illustrated cam system 23 rolls against said flat surfaces, thus causing a translation of the bearing part 24.

Other shapes may be envisaged for the cavity receiving the cam system.

In the present example, the bearing part 24 has a general parallelepiped shape comprising two large lateral faces, substantially parallel to the plane YZ, and four faces of lower surface area, that is to say of smaller surface area than the lateral surfaces. The cavity 242 extends substantially to the centre of said lateral faces of the bearing part 24.

Here, the two large lateral faces of the bearing part 24 are pierced. The cavity 242 is thus a through cavity. A length of the eccentric wheel along the direction X is substantially equal to a length of the bearing part along the direction X.

In an alternative, one of the two large lateral faces may not be pierced, such that the cavity 242 constitutes a blind hole. One advantage of a blind hole is to enable the confinement of a volume of anti-friction fluid inside the cavity 242. Thus, friction of the cam system 23 against the inner edge 241 may be attenuated while the valve 2 is in operation, which reduces the energy consumption of the valve.

The minimum width of the cavity 242 along the direction of translation Y is greater than the diameter of the circular base of the eccentric wheel. In the present example, said minimum width is substantially equal to the diameter of the circular base of the eccentric wheel, such that the longitudinal face of the eccentric wheel is in contact with the inner edge 241 of the bearing part.

In the present example, the valve base 21 comprises two sides 212 positioned in contact with the bearing part 24, to guide the bearing part in its translational movement with respect to the valve base. The two sides are placed on either side of the bearing part 24 with respect to the direction Z.

Each side 212 has a substantially flat inner face, forming a contact surface with an outer face of the bearing part 24. Said two inner faces of the sides 212 extend parallel to the plane XY.

Thus, the sides 212 form a guiding rail in which the bearing part 24 is intended to slide during its translational movement along the direction Y. One advantage of said guiding rail is to avoid the bearing part 24 drifting from its trajectory along the direction Y, during its translational movement.

In the example of FIGS. 1a to 1d, the two sides 212 have an "L" shape along a plane of section parallel to the plane XZ. Each side hugs the dimensions of the bearing part, namely a height of the side along the direction X and a length of the side along the direction Y are respectively equal to a height and a length of the bearing part.

Preferably, the cam system 23 (here the eccentric wheel) has a generally flat lateral face, extending in a plane parallel to the plane YZ, and a flange 29 is positioned along said lateral face. The role of the flange is described in detail hereafter.

Abutment Part

An abutment part 25 is mounted on the valve base 21 and is positioned at least partially opposite the bearing part 24 along the direction of translation Y. The abutment part 25 is distanced from the bearing part 24 along the direction Y. A minimum axial gap (in the maximum opening position of the valve) along the direction Y between the bearing part 24 and the abutment part 25 is preferably comprised between 2 millimetres and 20 millimetres, and even more preferentially comprised between 5 and 10 millimetres. Said minimum axial gap is preferably close to 7 millimetres.

A tube receiving space is thus defined between the bearing part 24 and the abutment part 25. In FIG. 1a, an extension along the direction Y of the tube receiving space is equal to the axial gap between a right face of the bearing part 24 and a left face of the abutment part 25.

The abutment part 25 here has a general parallelepiped shape with a substantially flat face 252, extending parallel to the plane XZ facing the bearing part 24.

Preferably, a height of the abutment part 25 along the direction X is substantially equal to a height of the bearing part 24 along the direction X. Thus, no matter the position of the tubing in the receiving space, the tubing may be compressed between the bearing part 24 and the face 252 of the abutment part 25.

In the example illustrated in FIGS. 1a to 1d, the abutment part 25 is fixed with respect to the valve base 21. Thus, when the bearing part 24 is translationally moved with respect to the valve base 21, this is also translationally moved with respect to the abutment part 25.

In an alternative example, the abutment part 25 could be moveably mounted on the valve base 21 in order to adapt a width of the tube receiving space.

One advantage is that tubings of different diameters could be used in association with the valve 2, making the valve 2 more modular.

For example, the abutment part 25 could be mounted translationally moveable on the valve base 21 along the direction of translation Y. The valve 2 could then further comprise return means, arranged to force the abutment part 25 in the direction of the bearing part 24. These return means could then be fixed to the valve base on the one hand, and to the abutment part on the other hand.

It is possible for example to employ a compression spring as return means.

Hereafter, "compression portion" designates the part of the bearing part 24 oriented facing the abutment part 25, intended to be brought closer to the abutment part during closing of the valve 2. The compression portion bears the reference 240 in the appended figures.

The compression portion 240 has a shape suitable for producing a compression of the tubing 3 when said portion is brought closer to the abutment part 25.

Thus, the regulating valve 2 may be designated by the alternative denomination "clamp". Indeed, the compression portion 240 and the abutment part 25 can pinch the wall of the tubing 3 while the valve 2 is in operation.

Preferably, the compression portion 240 projects with respect to the face of the bearing part 24 which is oriented towards the abutment part 25 along the direction of translation Y.

Thus, in the present example, the compression portion 240 has a general tip shape of which a summit is oriented towards the abutment part 25.

A tip shape of the compression portion 240 has the advantage of generating a concentration of contact forces on a reduced surface, during a compression of the outer wall of the tubing 3. Thus, the compression portion 240 deforms the tubing 3 more easily.

In an alternative, numerous other shapes of compression portion 240 may be envisaged, among which a V shape, W shape, several chevrons shape, wave shape, etc.

It is also possible to omit any projecting shape, such that an entire face of the bearing part 24 (in FIGS. 1a to 1d, the right face) would form the compression portion.

Returning to the present example, the compression portion 240 comprises a tip edge 243 (visible in the exploded view of FIG. 2) extending parallel to the direction X, perpendicularly to the longitudinal direction L of extension of the tubing 3. The tip edge 243 preferentially extends along the bearing part 24.

One advantage is that, when the bearing part 24 is brought closer in the direction of the tubing 3, the compression portion 240 (here the tip) bears over its whole length on the outer wall of the tubing 3. Notably, in the case where the valve 2 can reach a total closing position in which the flow rate of fluid within the tubing is zero, the tip edge is sufficiently long to compress the tubing 3 over its entire diameter.

In the case where the bearing part 24 has a compression portion projecting along the direction Y, the abutment part 25 may comprise an abutment portion positioned facing the compression portion along the direction Y, said abutment portion having a shape complementary to that of the compression portion. In the present example, the face 252 of the abutment portion could thus be replaced by a face having a chevron surface, such that the tip of the compression portion 240 can fit into the chevron surface during the closing of the valve.

According to another alternative to the example shown in FIGS. 1a to 1d, the abutment part 25 could comprise a projecting portion positioned facing the compression portion 240 along the direction Y, projecting with respect to the abutment part along the direction Y.

Indeed, it will be understood that one or the other among the bearing part 24 and the abutment part 25 can support a projecting portion. Furthermore, it is possible to position a projecting portion (for example tip shaped) on the abutment part 25 in the case where the latter is fixed with respect to the valve base 21, in order to limit wear of said projecting portion over repeated openings/closings of the valve.

In the present example, the bearing part 24 bearing the compression portion 240 may be changed easily when the compression portion becomes worn.

As has been seen above, the axial gap between the bearing part 24 and the abutment part 25 along the direction of translation Y of the bearing part 24 forms a space for receiving a tubing. This receiving space is thus confined along the direction Y; however, while the valve is in use, a tubing may be accidentally displaced along the direction X and come out of the receiving space.

A cover, also called flange 29, is preferentially added to the valve 2 to confine (in association with the valve base 21) the tube receiving space along the direction X, that is to say to obstruct at least partially access to the receiving space along the direction X.

Such a flange is typically positioned on a lateral face of the cam system 23, and is thus integral with the cam system 23 in its rotation around its axis of rotation B.

The flange 29 has a shape chosen to extend axially, along the direction Y, between the compression portion 240 and the abutment part 25, at least in a given range of angular position of the cam system around the axis B.

In the positions where the flange 29 extends axially between the compression portion 240 and the abutment part 25, the flange 29 thus prevents a too important displacement of the tubing 3 along the direction X which would cause an extraction of the tubing with respect to the receiving space.

The flange 29 thus obstructs the receiving space in a selective manner, as a function of the translational position of the bearing part 24.

In the present example, the flange 29 is formed of a thin sheet, for example made of polymer material or glass. It may be placed on the free lateral face of the eccentric wheel. The plate is for example screwed onto the eccentric wheel by a screw 215.

The flange 29 has two opposite faces, preferably flat and extending parallel to the plane YZ.

In the present example, the two faces of the flange 29 are of identical shape and composed of a rectangular portion (on the right of FIG. 1a) and a semi-circular portion (on the left of FIG. 1a). Said two faces thus comprise a straight edge and a rounded edge, opposite to one another. The rounded edge has a general "C" shape.

When said straight edge is aligned with the direction L of extension of the tubing, the receiving space is free and non-obstructed, and the tubing 3 is thus not blocked along the direction X (position of FIG. 1a).

When said straight edge is not aligned with the direction L, the flange 29 overlaps the receiving space, the receiving space thus being at least partially obstructed, and the tubing thus being blocked along the direction X.

The rounded edge is provided to rapidly block the tubing along the direction X during the translational displacement of the compression portion 240, from the maximum opening position and in the direction of the abutment part 25.

The flange may further have rounded corners on either side of the straight edge, which may be formed at the level of the angles of the rectangular portion for the example described above. One advantage of using a flange 29 having such rounded corners is that during the angular displacement of the cam system 23, the rounded corner entering into contact with the tubing 3 can push it towards the inside of the receiving space (that is to say here towards the valve base 21) along the direction X.

Further, to facilitate the assembly of the flange 29 during the manufacture of the valve 2, the cam system 23 may comprise a centring pin 293, and the flange 29 will comprise in this case a centring cavity 292 able to receive the centring pin 293.

Thus, the flange will be able to be correctly arranged with respect to the cam system and more generally correctly placed in the valve during the assembly of the valve.

In a preferential manner, when the valve 2 comprises a cover such as the flange 29, the abutment part 25 locally has a shape complementary with that of an edge of the cover. In the present example, the abutment part 25 has a shoulder 251 having a concave shape, of curvature similar to that of the rounded edge of the flange 29. In the position illustrated in FIG. 1d, the rounded edge of the flange 29 thus abuts against the abutment part 25.

Magnetic Sensor for Detecting the Position of the Regulating Valve

The regulating valve 2 further comprises a system for detecting the axial position of the bearing part 24 along the direction of translation Y.

The position of the bearing part along the direction Y makes it possible to deduce the position of the compression portion 240, and thus the compression state of the walls of the tubing 3.

In this respect, the system for detecting the angular position of the cam system 23 may comprise a magnetic sensor 281, associated with a magnet 280.

Figure 3A:
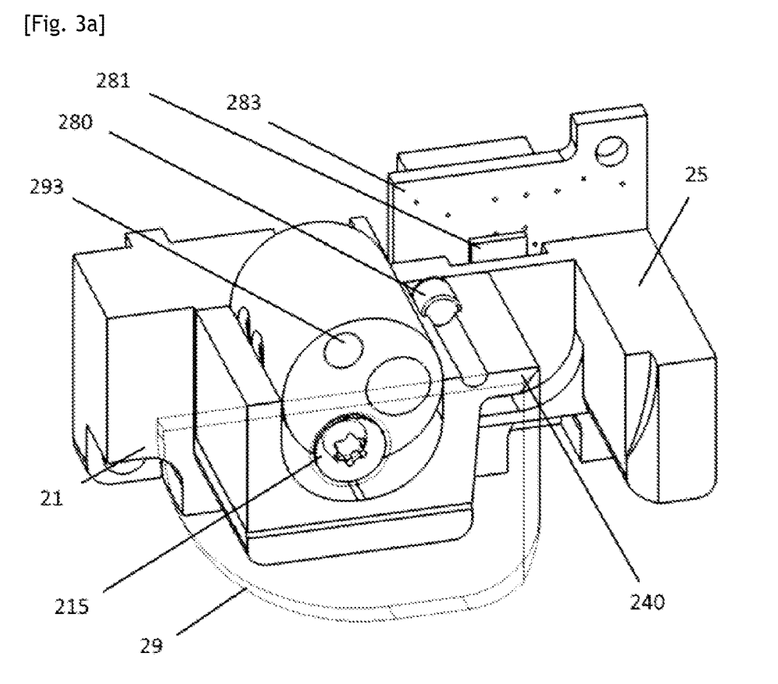
Figure 3B:
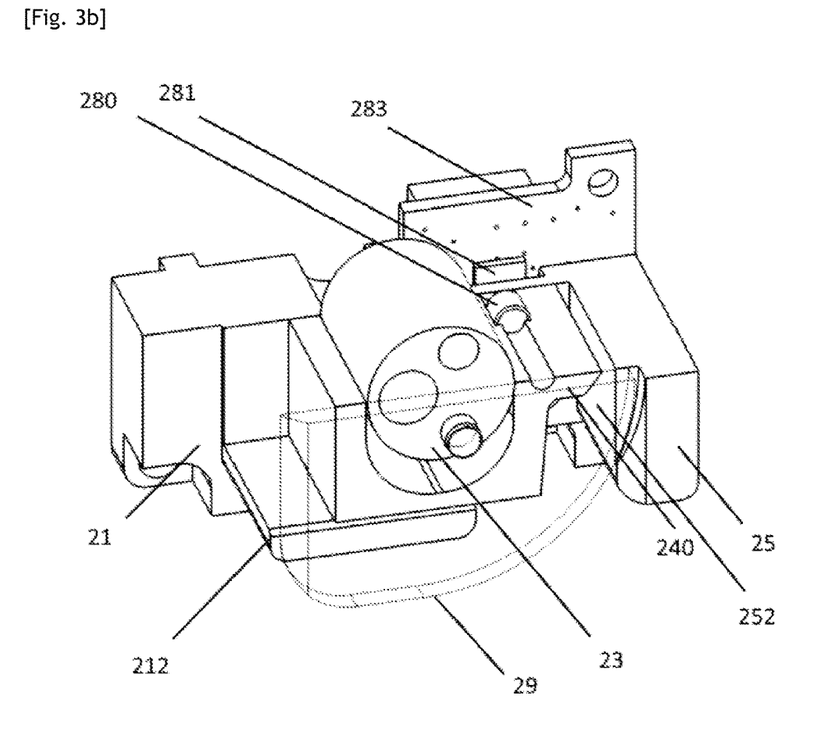
FIG. 3b is a partial perspective view of the regulating valve of FIG. 1a, wherein a portion of a valve base has been omitted to allow other elements to appear, this view corresponding to the state of the regulating valve in FIG. 1d.

The magnet 280 and the magnetic sensor 281 are visible in appended FIGS. 3a and 3b, giving a top view in partial section of the regulating valve 2 along a sectional plane AA parallel to the plane XY. The sectional plane AA constitutes a median plane for the tip of the compression portion 240.

FIG. 3a illustrates a maximum opening position of the regulating valve 2 (and corresponds to the view of FIG. 1a).

Figure 1B:
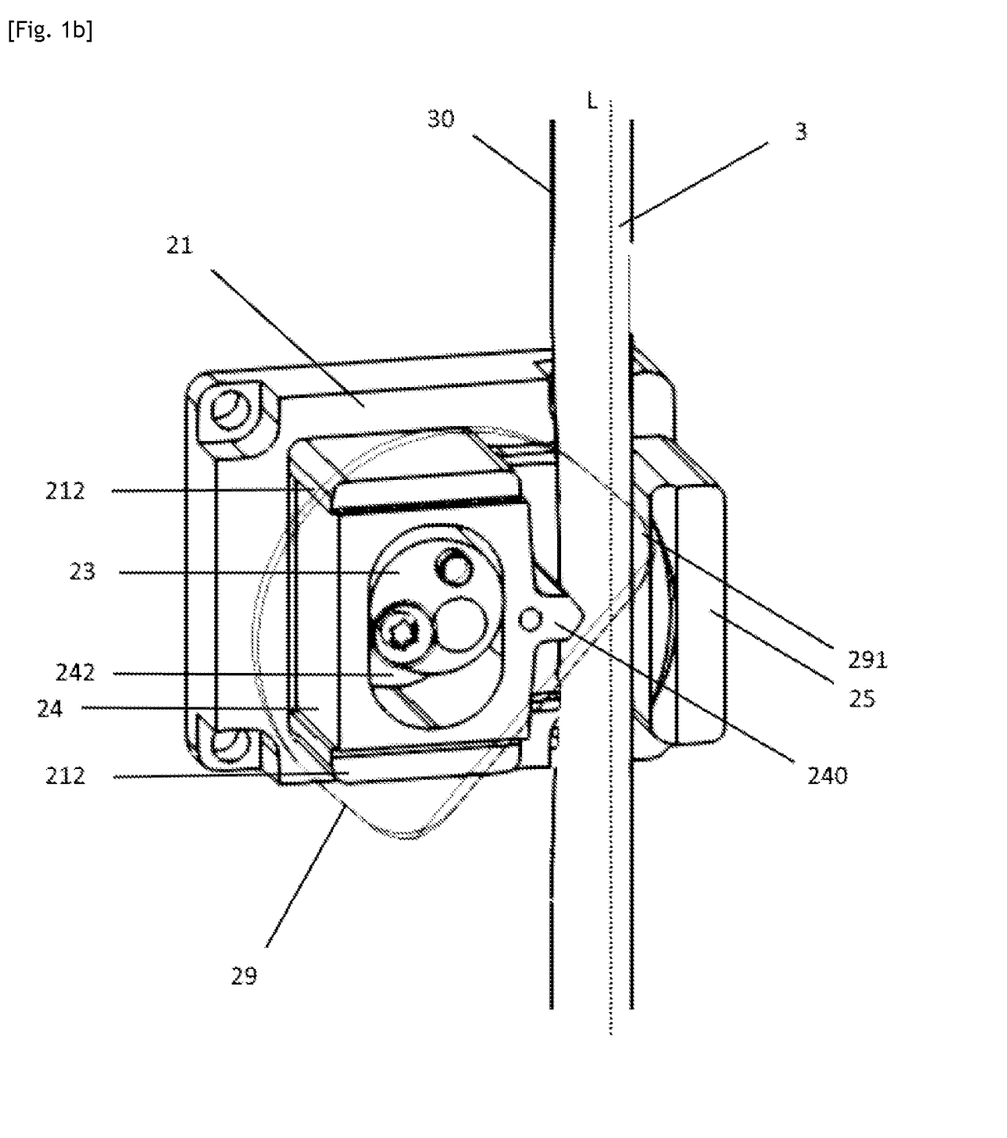
FIG. 1b is a perspective view of the regulating valve of FIG. 1a, in a state corresponding to a first intermediate travel position of the regulating valve.
Figure 1C:
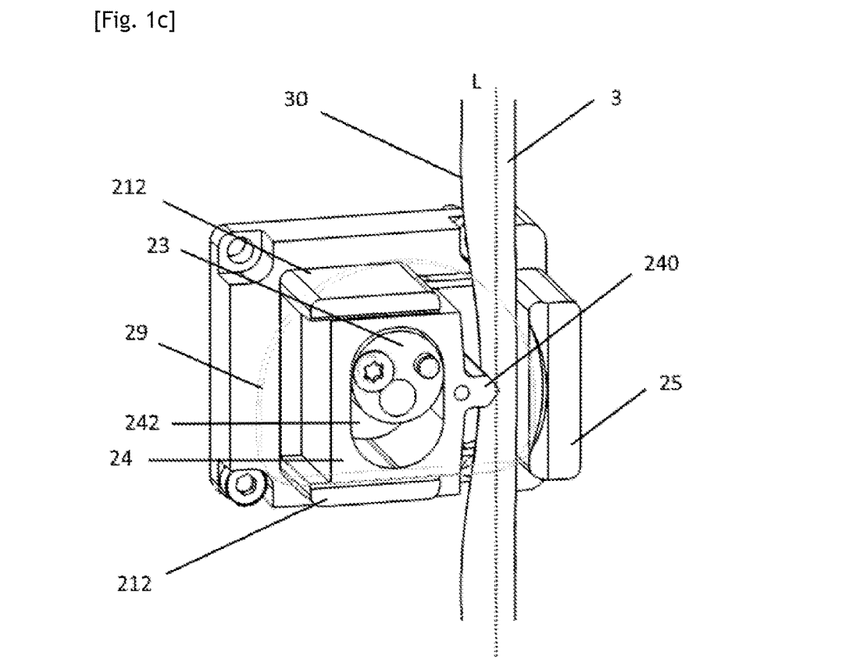
FIG. 1c is a perspective view of the regulating valve of FIG. 1a, in a state corresponding to a second intermediate travel position of the regulating valve.
Figure 1D:
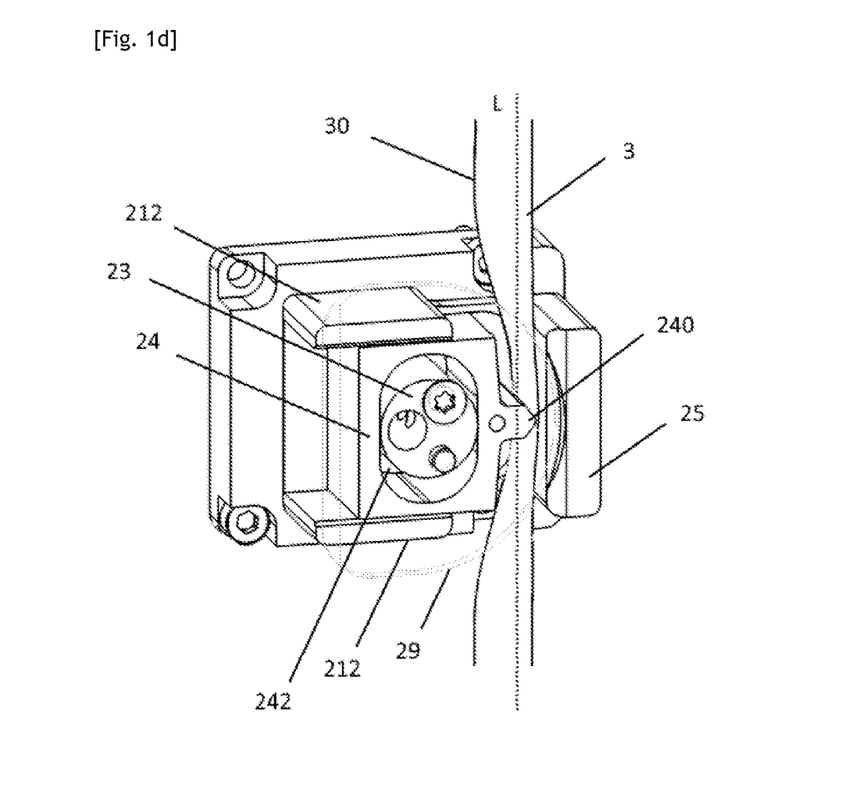
FIG. 1d is a perspective view of the regulating valve of FIG. 1a, in a state corresponding to a closed position of the regulating valve.

FIG. 3b illustrates a maximum closing position of the regulating valve 2 (and corresponds to the view of FIG. 1d).

The magnetic sensor 281 is an inductive sensor capable of detecting a magnetic field generated by the magnet 280. The magnet 280 is preferably a permanent magnet formed of a ferromagnetic material.

The magnet 280 is positioned with respect to the magnetic sensor 281 in such a way that the magnetic field detected by the sensor is variable as a function of the relative position of the sensor and the magnet along the direction of translation Y.

The magnetic sensor 281 is capable of detecting the magnetic field produced by the magnet 280, whatever the position of the latter. However, a position of the magnet 280 in the vicinity of the magnetic sensor 281 brings about the detection of a more important magnetic field than a position of the magnet 280 distant from the magnetic sensor 281.

In an advantageous manner, the magnetic sensor 281 is a Hall effect probe. Such a probe is in the form of a thin plate, of rectangular shape. A variation in magnetic field normal to the plate results in a variation in the electric signal at the terminals of the Hall effect probe.

In the present example, the magnetic sensor 281 is placed on a support circuit 283 arranged in the valve base 21. The plate of the Hall effect sensor is aligned along a plane substantially parallel to the plane YZ.

The magnet 280 is here a permanent magnet of substantially cylindrical shape and a longitudinal axis of the magnet 280 is perpendicular to the plane of the plate.

In the present example, the magnet 280 is integral with the bearing part 24 and the magnetic sensor 281 is integral with the valve base 21.

Indeed, the magnet 280 is placed inside the bearing part 24, here inside the tip of the compression portion 240. A channel extending along the direction X is provided inside the tip to accommodate the magnet 280.

In the position of FIG. 3a, the magnet 280 is axially distanced with respect to the magnetic sensor 281 along the direction of translation Y.

The magnetic field detected by the magnetic sensor 281 is not very intense.

In the position of FIG. 3b, the axial gap along the direction Y between the magnet 280 and the magnetic sensor 281 is reduced. A longitudinal axis of the magnet 280 is aligned with a central axis of the plate of the magnetic sensor 281.

The magnetic field detected by the magnetic sensor 281 is thus more intense than in the position illustrated in FIG. 3a.

In an alternative architecture, the magnet may be arranged integral with the valve base 21 and the magnetic sensor may be arranged integral with the bearing part 24.

In a further alternative manner, one among the magnet and the sensor may be arranged in the bearing part 24, and the other among the magnet and the sensor may be arranged in the abutment part 25.

The magnetic sensor 281 produces, while the valve 2 is in use, a magnetic field detection signal. This signal may be processed downstream to know the state of the valve and to control a parameter of opening/closing of the valve.

Whatever the chosen architecture, the magnetic sensor (notably the Hall effect probe) provides a simple and reliable means of knowing the translational position of the bearing part 24 along the direction of translation Y.

It will be understood that the Hall effect probe may be replaced or completed by another type of inductive sensor. More generally, it is possible to use any type of sensor enabling reliable detection of the position of the bearing part, or potentially a detection of the position of the abutment part 25 if the latter is moveable.

Example of Operation of the Regulating Valve

An exemplary calibration of the regulating valve, when being powered on, then an example of sequence of passage from an open state to a closed state of the regulating valve are described hereafter.

Before being powered on, the regulating valve is preferably in an open position. A tube receiving space is then available between the bearing part 24 and the abutment part 25.

For example, the valve 2 is in the state illustrated in FIG. 1a before being powered on. FIG. 1a corresponds to a maximum opening position. The axial gap between the compression portion and the abutment part is comprised between 2 millimetres and 20 millimetres, and is for example close to 7 millimetres.

In an advantageous manner, during the starting up of the valve (for example, during the activation of a unit for treating haemorrhagic liquid containing the valve), an initial value of magnetic field detected by the magnetic sensor 281 is saved in a memory, for example in a memory of a calculating unit 102. The initial magnetic field value is thus used to carry out a calibration of the sensor.

While the valve is in operation, the calculating unit 102 thus makes a comparison between a current value of the detected magnetic field and the initial value, in order to determine a translational displacement of the bearing part 24.

In an advantageous manner, the calibration of the sensor may be re-iterated at each change of tubing, from the moment that a new tubing is positioned in the receiving space, notably if this new tubing has dimensions distinct from the dimensions of a preceding tubing.

This thus avoids calculating erroneous values of the compression state of the walls of the tubing while the valve is in operation. The flow rate of liquid within the tubing can thus be deduced in real time in a reliable manner.

It will be noted that in the maximum opening position of FIG. 1a, the straight edge of the flange 29 is aligned with the longitudinal direction L of extension of the tubing. The axial position of the straight edge of the flange 29 is identical to the axial position of the abutment part 24, here at an axial position of the summit of the tip of the compression portion 240. The straight edge of the flange 29 could also be slightly set back axially with respect to the abutment part 24.

Generally speaking, in maximum opening position, the tube receiving space is free and thus not obstructed by the cover, this being arranged to not extend axially in the receiving space since it does not go beyond the abutment part 24 or the compression portion 240.

It is thus possible, in the maximum opening position of FIG. 1a, to remove the tubing 3 from the receiving space.

A sequence of use of the valve 2 is next described.

After the calibration, the bearing part 24 is preferentially displaced by the motor and by the cam system 23 to reach a position of engagement with the tubing 3. "Position of engagement" is taken to mean that the compression portion 240 is placed in contact with the outer wall 30 of the tubing, while not compressing or compressing very little the tubing. The flow rate of liquid within the tubing is thus unchanged.

As an example, the angular displacement of the cam system 23 between the maximum opening position and the position of engagement may be comprised between 5° and 45°.

FIG. 1b corresponds to such a position of engagement. The axial gap between the compression portion 240 and the abutment part 25 is then less than the axial gap in the maximum opening position.

It will be noted that the translational travel necessary in order that the bearing part 24 reaches such a position of "engagement" is variable as a function of the diameter of the outer wall of the tubing arranged in the tube receiving space.

Preferably, when the unit for treating haemorrhagic liquid is active, the bearing part 24 can be displaced between the position of engagement and the maximum closing position, these two latter positions forming extreme positions of the bearing part.

One advantage is that, in the position of engagement and in the maximum closing position, as well as in any intermediate position along the direction Y, the flange 29 prevents the tubing 3 accidentally coming out of the receiving space.

On the other hand, in the maximum opening position of the valve, the flange 29 does not prevent removal of the tubing, which makes it possible to change tubing while the unit for treating haemorrhagic liquid is not is use. When it is wished to reduce the flow rate of fluid within the tubing 3, the bearing part 24 is displaced by the motor and by the cam system 23, in the direction of the abutment part 25, to reach an intermediate travel position.

FIG. 1c illustrates such an intermediate travel position. The axial gap between the compression portion and the abutment part in the intermediate travel position is less than the axial gap in the position of engagement. It is also less than the outer diameter of the tubing 3. Thus, the inner section of the tubing 3 is decreased by compression of the walls of the tubing, but without totally cancelling the flow rate of fluid.

When it is wished to cancel completely the flow rate of fluid and reach a closed position of the valve 2, the bearing part 24 is displaced even further in the direction of the abutment part 25 by the motor and by the cam system 23, to reach a maximum closing position.

FIG. 1d illustrates such a maximum closing position. The axial gap between the compression portion and the abutment part in the maximum closing position is less than the axial gap in the intermediate travel position.

As illustrated in FIG. 1d, the outer wall 30 of the tubing 3 is pinched, in the maximum closing position, between the abutment part 25 and the compression portion 240. Fluid, for example haemorrhagic liquid, cannot traverse the tubing.

As an example, the angular displacement of the cam system 23 between the maximum opening position and the maximum closing position may be comprised between 90° and 270° and is notably, preferably, of the order of 180°.

It will be noted that the bearing part 24 may be stabilised at any position along the direction of translation Y between the maximum closing position and the maximum opening position. The valve being able to be stabilised in any of these positions, it is possible to regulate the flow rate of fluid through the tube in a controlled manner, for a desired duration.

Notably, the valve, and in particular the bearing part 24, may be stabilised in any position among the maximum opening position of FIG. 1a, the position of engagement of FIG. 1b, the intermediate travel position of FIG. 1c, and the maximum closing position of FIG. 1d.

Thus, the position of engagement and the intermediate travel position are not uniquely transitory positions of the bearing part 24 during a displacement between the maximum opening position and the maximum closing position. It is possible that the valve is stabilised in one of these two positions. It is also possible that the bearing part 24 passes in a transitory manner through one and/or the other of these positions, during a direct movement. This depends on the command transmitted to the valve.

It will be understood that the sequence of displacement described above is reversible. Thus, it is possible to return as desired to any of the positions described above, or reach another intermediate position of the bearing part 24 along the direction Y.

One of the particularities of the regulating valve described is in fact that it may be stabilised in any intermediate position between the open position where the flow is maximal, and the closed position where the flux is zero.

System for Treating Haemorrhagic Liquid

Figure 4:
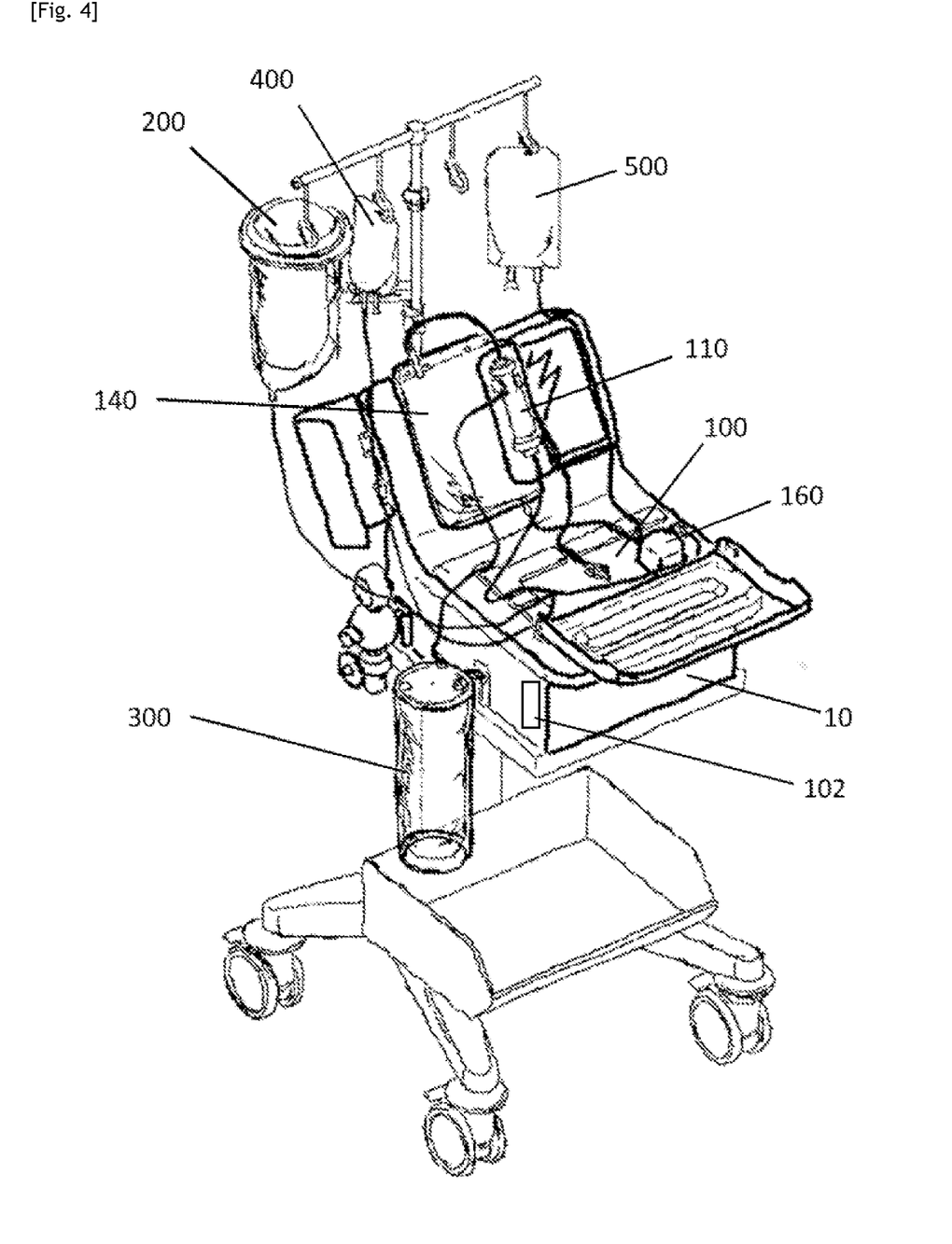
FIG. 4 illustrates a system for treating haemorrhagic liquid with a view to an autotransfusion, according to an exemplary embodiment.

In appended FIG. 4 is represented a system for treating haemorrhagic liquid according to an example. The treatment system can be used during an intervention on a patient, in order to carry out a blood autotransfusion. The treated haemorrhagic liquid is preferentially blood.

The treatment system comprises a unit for treating haemorrhagic liquid 100, which will be described in greater detail in relation with FIG. 5. The treatment system according to this example also comprises a collection unit 200 making it possible to collect the haemorrhagic liquid initially taken from the patient, a recovery unit 300 intended to recover the filtrate coming from the treatment of the haemorrhagic liquid, a transfusion unit 400 coupled to a transfusion line of the treatment unit 100, and a dilution unit 500 coupled to a dilution line of the treatment unit 100.

The treatment system according to this example further preferably comprises and as illustrated in FIG. 4, a support unit 10 comprising a main support body mounted on roulettes.

The support unit 10 integrates data processing means, for example one or more processors.

The support unit 10 notably comprises, preferably, a calculating unit 102 configured to control a parameter for opening/closing at least one regulating valve, as a function of the detection signal of the magnetic field generated by a magnetic sensor of this regulating valve (for example the magnetic sensor 281).

In a preferred manner, the calculating unit 102 is configured to save in a memory, during a starting up phase, an initial value of said magnetic field detection signal. The calculating unit thus participates in a calibration of the measurement of the parameter for opening/closing the regulating valve.

Next, during a later phase of operation of the treatment unit 100, the calculating unit 102 determines the parameter for opening/closing the regulating valve as a function of the initial value of the magnetic field detection signal.

Preferably, the calculating unit 102 is able to control the opening/closing of each of the regulating valves of the system, as a function of the detection signals of magnetic fields generated by their respective magnetic sensors.

The support unit 10 also integrates, preferably, command means making it possible to control the treatment of the haemorrhagic liquid as a function of predetermined treatment parameters and/or as a function of command information entered by the user of the system.

In this respect, the support unit 10 may include command information capture means, such as a keyboard, tactile actuators, a voice recognition system, or others. Preferably, means for displaying information to the user, for example a screen provided with a graphic interface, are also provided.

The circulation of liquids in the treatment system is achieved by liquid drive means, which are integrated in the support unit 10 or are external.

The support unit 10 also integrates, preferably, means for supplying the treatment system with energy, notably electrical energy.

Preferably, the support unit 10 also integrates non-consumable elements of the system for treating haemorrhagic liquid, that is to say elements that are able to be reused during several successive haemorrhagic liquid treatment cycles. They may be in particular elements of the system not being in direct contact with the haemorrhagic liquid of the patient, or with any other substance that could lead to contaminations.

Figure 5:
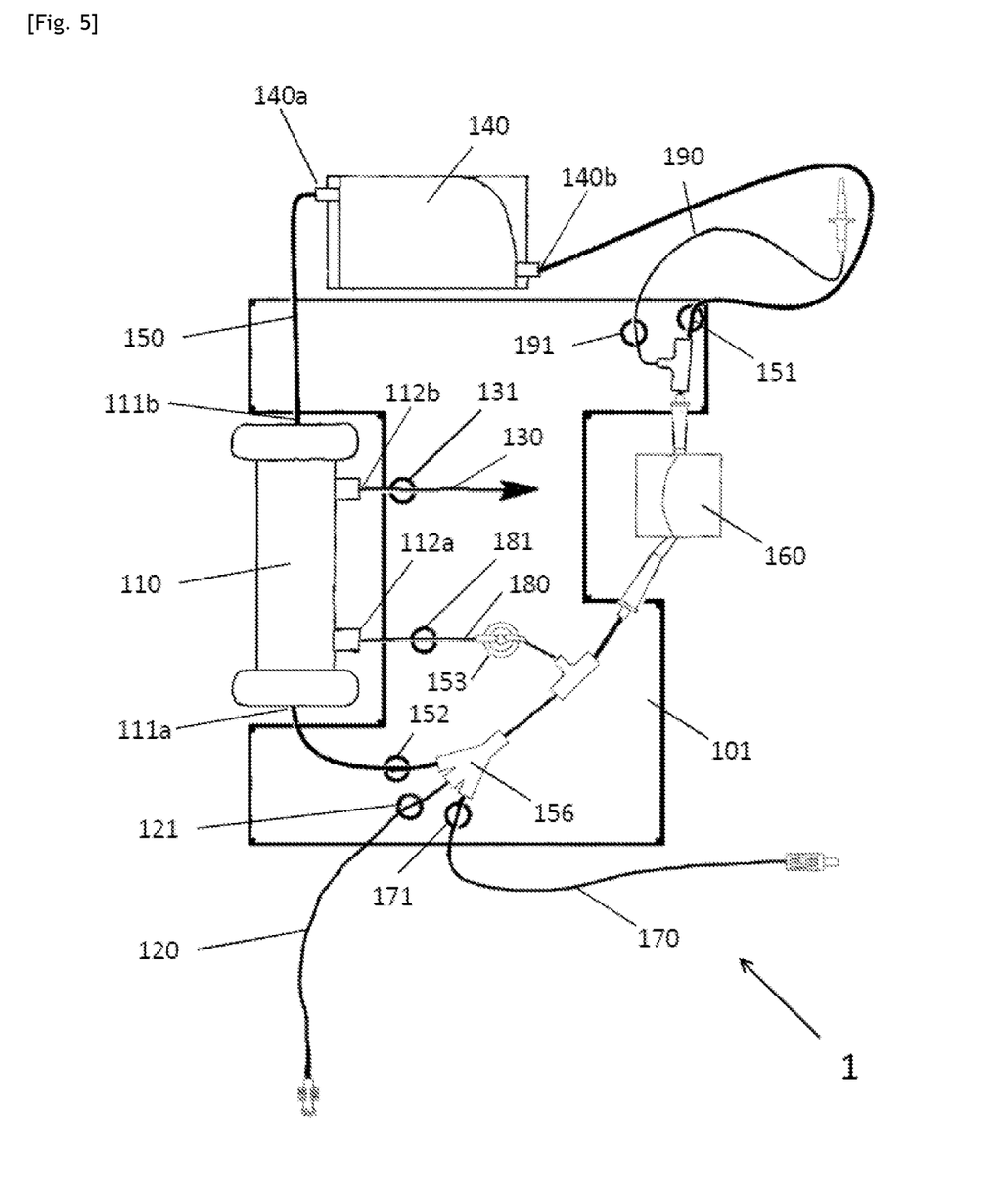
FIG. 5 illustrates an exemplary unit for treating haemorrhagic liquid being able to be included in the treatment system illustrated in FIG. 4, this treatment unit comprising several liquid flow rate regulating valves in order to control the flows of haemorrhagic liquid.

FIG. 5 illustrates a unit for treating haemorrhagic liquid 100 according to an example. Said treatment unit 100 may be integrated in the system of FIG. 4.

The treatment unit 100 notably comprises a filtration device 110, an intake line 120, a discharge line 130, a treatment bag 140 provided with a bag inlet 140a and a bag outlet 140b, a recirculation line 150, pumping means 160

(preferably a peristaltic pump), a transfusion line 170, a cleaning line 180 and a dilution line 190.

The intake 120, discharge 130, recirculation 150, transfusion 170, cleaning 180 and dilution 190 lines are fluid transfer lines comprising a tubing enabling the circulation of fluid, notably the circulation of haemorrhagic liquid such as blood, or instead the circulation of cleaning liquid.

In a highly advantageous and preferential manner, each fluid transfer line is provided with at least one liquid flow rate regulating valve, for example a regulating valve according to the embodiment described above in relation with FIGS. 1a to 3b.

Each of the regulating valves is intended to regulate a flow rate of liquid in the fluid transfer line with which said valve is associated.

In the present example, the intake 120, discharge 130, recirculation 150, transfusion 170, cleaning 180 and dilution 190 lines respectively comprise a valve 121, a valve 131, a valve 151, a valve 161, a valve 171, a valve 181 and a valve 191.

In the example of FIG. 5, the filtration device 110 has a fluid inlet 111a and a fluid outlet 111b, and an intake chamber having a chamber inlet 112a and a chamber outlet 112b.

The haemorrhagic liquid to treat circulates in the intake chamber 111 from the fluid inlet 111a to the fluid outlet 111b and undergoes a tangential filtration through a filtration membrane, in order to remove from the haemorrhagic liquid a filtrate comprising compounds undesired for the autotransfusion. The filtrate traverses the filtration membrane until reaching the discharge chamber 112.

In a preferred manner, the treatment unit 100 further comprises a pressure sensor 153 positioned within the circulation line 150, notably arranged to detect overpressures downstream of the pumping means 160.

In a preferred manner, the treatment unit 100 further comprises a multipath fluidic connector 156, in order to tap into the intake line 120 and the transfusion line 170 at the same position on the recirculation line 150, as illustrated in FIG. 5.

The treatment unit 100 further has, in a preferential manner, a template 101 provided for a specific placement on the support unit 10. For example, the template 101 is vertical and is provided to be positioned perpendicularly to a horizontal support plane of the support unit 10.

The treatment system of FIG. 4 can be used for treating a haemorrhagic liquid taken beforehand from a patient. The filtration device 110 makes it possible to treat an incoming volume of haemorrhagic liquid. The treatment bag 140 enables a recirculation of the haemorrhagic liquid during a treatment cycle, that is to say during several successive circulations in the filtration device. The treatment bag 140 may also be employed as zone for mixing the haemorrhagic liquid to treat with a dilution liquid, in order to favour the filtration and the elimination of soluble elements such as proteins and medicinal substances.

Finally, the dilution line 190 makes it possible to dilute the treated haemorrhagic liquid, in view of its reinjection into the patient to perform the autotransfusion operation.

In a preferred manner, a dilution may be carried out by obstructing the outlet of the treatment bag 140 at the level of the first regulating valve 151, then by injecting cleaning liquid into the intake chamber of the filtration device 110, from the dilution line 190. The treated haemorrhagic liquid present in the treatment bag 140 may next be isolated when the haemorrhagic liquid present in the recirculation line 150 has a haematocrit level below a threshold value.

When it is wished to carry out a transfusion into the patient, it is appropriate to disconnect the transfusion unit 400 from the treatment system and to connect it to the patient, for transfusion of the treated haemorrhagic liquid.

For further details concerning the operation of the treatment unit 100 and the use of other functional units of the treatment system, reference may be made to the documents published under the references WO 2019/129973 A1 and WO 2019/129974 A1.

Although the above description relates to liquid flow regulating valves integrated in a system for treating haemorrhagic liquid with a view to autotransfusion, it will be understood that the regulating valve of the invention may be integrated, with the same advantages, in a system other than a treatment system with a view to autotransfusion. In particular, a regulating valve conforming to the invention may be used to regulate the flow rate of a fluid different from a haemorrhagic liquid.

The invention claimed is:

1. An automatic valve for regulating a flow rate of liquid intended to circulate in a flexible tube, the regulating valve comprising:
a valve base,
a cam system arranged to be rotationally driven by a drive shaft of a motor, the cam system being moveably mounted on the valve base to rotate around an axis of rotation (B),
a bearing part translationally mounted on the valve base, the bearing part being arranged to be translationally moved with respect to the valve base along a direction of translation (Y) following a rotational movement of the cam system, the bearing part comprising a compression portion,
an abutment part mounted on the valve base and positioned opposite the compression portion along the direction of translation (Y), such that the abutment part and the bearing part define between them a receiving space extending along a longitudinal direction (L) and intended to receive a flexible tube, the translation of the bearing part displacing the compression portion along the direction of translation (Y), in order to modify a dimension along the direction of translation of the receiving space between the bearing part and the abutment part,
wherein the bearing part is translationally moveable along the direction of translation (Y) between the following two positions:
a close together position, wherein the dimension of the receiving space along the direction of translation (Y) is equal to a first distance,
a spaced apart position, wherein the dimension of the receiving space along the direction of translation (Y) is equal to a second distance strictly greater than the first distance,
the bearing part being configured to be stabilised in any intermediate position situated between the close together position and the spaced apart position,
the valve further comprising a magnet integral with the bearing part or with the valve base, and a magnetic sensor integral respectively with the valve base or with the bearing part, the magnetic sensor being arranged to detect a magnetic field generated by the magnet whatever the position of the bearing part, and
the valve further comprising a cover intended to obstruct the receiving space as a function of the position of the bearing part.

2. The valve of claim 1, wherein the cam system comprises a cylindrical member rotationally mounted around the axis of rotation (B) and having an axis of revolution (A) different from the axis of rotation (B).

3. The valve of claim 1, wherein the bearing part comprises an inner wall defining a cavity, the cavity being provided to receive the cam system bearing against the inner wall.

4. The valve of claim 1, wherein the compression portion projects with respect to the bearing part along the direction of translation (Y).

5. The valve of claim 1, wherein the compression portion has a tip shape, and comprises a tip edge extending perpendicularly to the longitudinal direction (L) and perpendicularly to the direction of translation (Y).

6. The valve of claim 1, wherein the magnet is positioned inside the bearing part.

7. The valve of claim 6, wherein the magnet extends along a direction of extension perpendicular to the direction of translation (Y) of the bearing part.

8. The valve of claim 1, wherein the magnet is a permanent magnet formed of a ferromagnetic material.

9. The valve of claim 1, wherein the magnetic sensor comprises a Hall effect probe comprising a thin plate.

10. The valve of claim 9, wherein the magnet extends along a direction of extension perpendicular to a plane of extension of the thin plate.

11. The valve of claim 1, wherein the abutment part comprises an abutment portion positioned facing the compression portion along the direction of translation (Y), the compression portion and the abutment portion having surfaces of complementary shape.

12. The valve of claim 1, wherein the abutment part comprises a projecting portion positioned facing the compression portion along the direction of translation, said projecting portion projecting with respect to the abutment part along the direction of translation.

13. The valve of claim 1, wherein the abutment part is translationally mounted on the valve base along the direction of translation.

14. The valve of claim 1, wherein the valve base comprises two sides positioned opposite one another, said sides forming a guiding rail in which the bearing part is arranged to slide.

15. The valve of claim 1, wherein the cam system comprises a lateral face extending in a plane perpendicular to the axis of rotation (B) of the cam system, the cover being fixed on the lateral face.

16. The valve of claim 1, wherein the cover comprises at least one straight edge and further comprises at least one rounded edge.

17. The valve of claim 1, wherein, in the spaced apart position, the cover is positioned axially set back with respect to or flush with the compression portion along the direction of translation (Y), so as not to obstruct the receiving space.

18. The valve of claim 1, wherein the bearing part is translationally moveable along the direction of translation (Y) from the spaced apart position or from the close together position, to reach an intermediate travel position, wherein the dimension of the receiving space along the direction of translation (Y) is equal to a third distance comprised between the first distance and the second distance, the bearing part being configured to be stabilised in the intermediate travel position.

19. The valve of claim 18, wherein, in any position between the intermediate travel position and the close together position, the cover extends at least partially onto an axial extension comprised between the compression portion and the abutment part along the direction of translation (Y), so as to obstruct at least partially the receiving space.

20. The valve of claim 18, wherein the bearing part is translationally moveable along the direction of translation (Y) from the intermediate travel position or from the spaced apart position, to reach a supplementary intermediate travel position, situated between the intermediate travel position and the spaced apart position, the bearing part being configured to be stabilised in the supplementary intermediate travel position.

21. A treatment unit for treating a hemorrhagic liquid taken from a patient with a view to an autotransfusion, the treatment unit comprising:

a filtration device configured to treat a haemorrhagic liquid by removing undesirable compounds from the haemorrhagic liquid, a treatment bag configured to contain a treated haemorrhagic liquid, at least one fluid transfer line enabling a circulation of fluid, the fluid transfer line fluidically connecting one among the filtration device and the treatment bag to a fluid inlet, or to a fluid outlet, or to the other among the filtration device and the treatment bag, the fluid transfer line being provided with at least one regulating valve arranged for a regulation of a flow rate of liquid in the fluid transfer line, wherein the regulating valve comprises:

a valve base, a cam system arranged to be rotationally driven by a drive shaft of a motor, the cam system being moveably mounted on the valve base to rotate around an axis of rotation (B), a bearing part translationally mounted on the valve base, the bearing part being arranged to be translationally moved with respect to the valve base along a direction of translation (Y) following a rotational movement of the cam system, the bearing part comprising a compression portion, an abutment part mounted on the valve base and positioned opposite the compression portion along the direction of translation (Y), such that the abutment part and the bearing part define between them a receiving space extending along a longitudinal direction (L) and intended to receive a flexible tube, the translation of the bearing part displacing the compression portion along the direction of translation (Y), in order to modify a dimension along the direction of translation of the receiving space between the bearing part and the abutment part, wherein the bearing part is translationally moveable along the direction of translation (Y) between the following two positions:

a close together position, wherein the dimension of the receiving space along the direction of translation (Y) is equal to a first distance, a spaced apart position, wherein the dimension of the receiving space along the direction of translation (Y) is equal to a second distance strictly greater than the first distance, the bearing part being configured to be stabilised in any intermediate position situated between the close together position and the spaced apart position, the valve further comprising a magnet integral with the bearing part or with the valve base, and a magnetic sensor integral respectively with the valve base or with the bearing part, the magnetic sensor being arranged to detect a magnetic field generated by the magnet whatever the position of the bearing part, and the valve further comprising a cover intended to obstruct the receiving space as a function of the position of the bearing part.

22. The treatment unit of claim 21, comprising several fluid transfer lines comprising at least one valve for regulating the flow rate of liquid, said fluid transfer lines being chosen from among: an intake line, a discharge line, a recirculation line, a transfusion line, a cleaning line, and a dilution line.

23. The treatment unit of claim 21, the magnetic sensor of the regulating valve being configured to produce a magnetic field detection signal, the treatment unit further comprising a calculating unit configured to control a parameter of opening/closing of the regulating valve as a function of the magnetic field detection signal.

24. The treatment unit of claim 23, wherein the calculating unit is configured to save in a memory, during a phase of starting up the treatment unit, an initial value of the magnetic field detection signal, the calculating unit being further configured to determine the opening/closing parameter as a function of said initial value during a later phase of operation of the treatment unit.

* * * * *